US009763871B2

(12) United States Patent
Saito et al.

(10) Patent No.: US 9,763,871 B2
(45) Date of Patent: *Sep. 19, 2017

(54) HAIR COSMETIC COMPOSITION

(71) Applicant: KAO CORPORATION, Tokyo (JP)

(72) Inventors: Hiroaki Saito, Matsudo (JP); Chie Sakaguchi, Chiyoda-ku (JP); Kana Tsumura, Wakayama (JP)

(73) Assignee: KAO CORPORATION, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/035,954

(22) PCT Filed: Nov. 11, 2014

(86) PCT No.: PCT/JP2014/079792
§ 371 (c)(1),
(2) Date: May 11, 2016

(87) PCT Pub. No.: WO2015/072435
PCT Pub. Date: May 21, 2015

(65) Prior Publication Data
US 2016/0263009 A1  Sep. 15, 2016

(30) Foreign Application Priority Data

Nov. 15, 2013  (JP) ................. 2013-237345

(51) Int. Cl.
| A61Q 5/06 | (2006.01) |
| A61K 8/86 | (2006.01) |
| A61K 8/81 | (2006.01) |
| A61K 8/90 | (2006.01) |
| A45D 7/04 | (2006.01) |
| A45D 7/06 | (2006.01) |

(52) U.S. Cl.
CPC ............... *A61K 8/86* (2013.01); *A45D 7/04* (2013.01); *A45D 7/06* (2013.01); *A61K 8/8147* (2013.01); *A61K 8/90* (2013.01); *A61Q 5/06* (2013.01); *A61K 2800/594* (2013.01)

(58) Field of Classification Search
CPC .. A61K 2800/594; A61K 8/8152; A61K 8/86; A61Q 5/06
See application file for complete search history.

(56) References Cited

U.S. PATENT DOCUMENTS

| 5,989,570 | A | 11/1999 | Lion et al. | |
| 6,946,436 | B2* | 9/2005 | Wakamatsu | A61K 8/062 424/400 |
| 2012/0039834 | A1 | 2/2012 | Oshika et al. | |
| 2012/0164092 | A1 | 6/2012 | Kurashima et al. | |
| 2015/0150778 | A1 | 6/2015 | Ooshika et al. | |

FOREIGN PATENT DOCUMENTS

| JP | 10-072310 A | 3/1998 | |
| JP | 2986273 B2 | 12/1999 | |
| JP | 2000-204025 A | 7/2000 | |
| JP | 2001-507368 A | 6/2001 | |
| JP | 2003-012467 A | 1/2003 | |
| JP | 2003/113053 A | 4/2003 | |
| JP | 2007-106678 A | 4/2007 | |
| JP | 2010-126523 A | 6/2010 | |
| JP | 2010-168294 A | 8/2010 | |
| JP | 2010-275291 A | 12/2010 | |
| JP | 2012-006915 A | 1/2012 | |
| JP | 2013-256495 A | 12/2013 | |
| WO | 98/48771 A1 | 11/1998 | |
| WO | WO 2009090558 | * 7/2009 | ............... A61K 9/00 |
| WO | 2013/172475 A2 | 11/2013 | |
| WO | WO 2013/172475 A2 | 11/2013 | |
| WO | WO 2013/172475 A3 | 11/2013 | |

OTHER PUBLICATIONS

Barel et al. (Handbook of Cosmetic Science and Technology 2005, 2nd Ed., CRC Press: p. 512).*
Personal Care Magazine (Sep. 2012 [online] retrieved on Jan. 17, 2017 from: http://www.personalcaremagazine.com/story/10235/applications-of-acrylic-polymers-and-copolymers; 4 pages).*
Ekpenyong (Journal of Chemical Education, 1985; 62(2): pp. 173-174).*
Signori (Cosmetic Science Technology 2006: p. 219; 1 page).*
Ravindran et al. (Malaysian Journal of Pharmaceutical Sciences (2012;10(1):61-73; filed Sep. 29, 2015 in U.S. Appl. No. 14/387,733).*
ISR and Written Opinion (filed Sep. 24, 2014 in U.S. Appl. No. 14/387,733 reference AZ).*
Pluracare L/F Grades Poloxamer (filed Sep. 24, 2014 in U.S. Appl. No. 14/387,73 reference AX).*
International Search Report issued on Feb. 17, 2015 for PCT/JP2014/079792 filed on Nov. 11, 2014.
Extended European Search Report issued on Apr. 20, 2017 in Patent Application No. 14861881.2.

* cited by examiner

*Primary Examiner* — Ernst V Arnold
(74) *Attorney, Agent, or Firm* — Oblon, McClelland, Maier & Neustadt, L.L.P.

(57) ABSTRACT

A hair cosmetic composition comprising the following components (A), (B) and water, having a pH of 6 or less, and the component (B) being dispersed in a water phase:

(A) an oxyalkylene polymer represented by formula —(AO)$_n$— wherein A represents a $C_{2-6}$ alkylene group and n represents a number of 50 to 30,000, provided that n pieces of AO comprise at least two alkyleneoxy groups, which are arranged through either random polymerization or block polymerization; and (B) a polymer comprising a constitutional unit represented by the following formula (b1) and a constitutional unit represented by the following formula (b2), having a weight average molecular weight of 5,000 to 1,000,000, and having an acid value of 5 to 400:

$$-(CH_2CR^1COOH)- \quad (b1)$$

$$-(CH_2CR^2COOR^3)- \quad (b2)$$

wherein $R^1$ and $R^2$ represent H or $CH_3$, and $R^3$ represents a $C_{1-30}$ hydrocarbon group.

12 Claims, No Drawings

HAIR COSMETIC COMPOSITION

FIELD OF THE INVENTION

The present invention relates to a hair cosmetic composition comprising specific polymers.

BACKGROUND OF THE INVENTION

In a recent hair styling agent, an amount of an adhesive polymer or a set polymer forming a rigid film is generally increasing for improving hairstyle set retention, so as to improve fixing a hairstyle by adhesiveness derived from the polymer or the rigid polymer film.

A hair styling agent containing a large amount of an adhesive polymer can set a hairstyle by adhering hairs to one another by adhesiveness of the polymer, and can provide stable hair styling, however, such a polymer shows strong stickiness and makes it difficult to keep natural feel of hair in many cases, which is a problem to be solved. On the other hand, a hair styling agent forming a rigid film for providing a styling performance and durability thereof shows less stickiness, however shows stiffness because of forming a rigid film for hairstyle retention, therefore, insufficient in terms of providing hair with natural feel. Accordingly, it is desired not only to set and keep a desired hairstyle but also to keep natural feel of hair without imparting stiffness and stickiness.

Besides, in order to comply with unprecedented needs for enabling hairstyling without wetting the hair with water or using additional hair styling agent even when away from home or office, a hair styling agent showing excellent durability as well as restyling ability is strongly requested. In other words, a hair styling agent capable of rigidly retaining a hairstyle with natural feels, and further of freely restyling hair, is requested.

For example, Patent Document 1 proposes a hair cosmetic composition capable of restyling hair by using a specific set polymer.

Patent Document 2 proposes a hairstyling cosmetic composition containing, in a specific ratio, (a) polyalkylene glycol in a solid form, (b) alcohol in a liquid form, an alkylene oxide addition polymer of alcohol or carboxylic acid, or a polyalkylene glycol polymer, (c) a film forming polymer and (d) sugar alcohol. This hairstyling cosmetic composition is known to provide restyling ability as well as to have improved hair setting ability.

Furthermore, Patent Document 3 discloses, for example, a technique to obtain a hair cosmetic composition showing excellent hair setting performance and restyling performance by adding, to a specific hair set polymer, polyalkylene glycol in a substantially equivalent amount for providing adhesiveness.

On the other hand, in order to avoid stickiness of a hair cosmetic composition containing a set polymer, the hair cosmetic composition has been conventionally generally improved by adding an oil component or a nonvolatile solvent for improving lubrication properties. When such a component is added, however, the hair set performance or the restyling performance may be lowered. As a countermeasure, there is a technique to avoid the stickiness of a hair cosmetic composition as well as to improve the hair set performance and the restyling performance, which were not simultaneously attained in the conventional techniques (see Patent Document 4). According to this disclosure, a polymer showing adhesiveness characterized in that both strong adhesion to the polymer itself (hereinafter referred to as the "self-adhesive force") and weak adhesion to the other object (hereinafter referred to as the "adhesive force to other") (such an adhesiveness will be hereinafter referred to as "self-selective-adhesiveness") is incorporated in a hair cosmetic composition, so as to provide sufficient hair set performance and restyling performance and also to avoid stickiness and stiffness.

(Patent Document 1) JP-A-2001-507368
(Patent Document 2) JP-A-2010-275291
(Patent Document 3) JP-A-2010-126523
(Patent Document 4) JP-A-2010-168294

SUMMARY OF THE INVENTION

The present invention provides a hair cosmetic composition comprising the following components (A), (B) and water, having a pH at 25° C. of 6 or less, and the component (B) being dispersed in a water phase.

(A) an oxyalkylene polymer represented by the following formula (a1):

—(AO)$_n$—  (a1)

wherein A represents an alkylene group having 2 to 6 carbon atoms and n represents a number of 50 or more and 30,000 or less, provided that n pieces of AO consists of at least two alkyleneoxy groups, which are arranged through either random polymerization or block polymerization; and (B) a polymer comprising a constitutional unit represented by the following formula (b1) and a constitutional unit represented by the following formula (b2), having a weight average molecular weight of 5,000 or more and 1,000,000 or less, and an acid value of 5 or more and 400 or less:

—(CH$_2$CR$^1$COOH)—  (b1)

—(CH$_2$CR$^2$COOR$^3$)—  (b2)

wherein R$^1$ and R$^2$ represent a hydrogen atom or a methyl group and R$^3$ represents a hydrocarbon group having 1 or more and 30 or less carbon atoms.

The present invention further provides a hair styling method for setting a hairstyle by applying the above-described hair cosmetic composition to hair.

The present invention further provides use of the above-described hair cosmetic composition as a hair styling agent.

DETAILED DESCRIPTION OF THE INVENTION

The hair cosmetic composition of Patent Document 4 shows high adhesiveness to strongly adhere hairs to one another immediately after applying it to the hair, and hence, it is difficult to deliberately set a hairstyle. For example, hair styling method in which the hair is set with using a hair brush while blowing the hair with warm air from a hair dryer cannot be performed by using the hair cosmetic composition.

Accordingly, the present invention relates to provision of a hair cosmetic composition which shows adhesive force at an appropriate timing when dried, is free from stickiness and stiffness, and has sufficient hair set performance and restyling performance, so that a hairstyle can be deliberately set even in setting the hair with using, for example, a hair dryer.

The present inventors have found the that, by combining an oxyalkylene polymer having a specific structure with a (meth)acrylic acid-based polymer having a specific structure and a specific acid value in an acid state, and adjusting a pH in a water phase set to 6 or less, the latter (meth)acrylic acid-based polymer may be dispersed in the water phase, and after application thereof to hair, expression of adhesive force through drying may be delayed so that a time for deliberately setting a hairstyle can be certainly obtained. In addition, the inventors have also found that, the oxyalkylene polymer and the (meth)acrylic acid-based polymer contained in the composition are mutually mixed during drying to form a uniform transparent film on hairs, and hence can work as a hair cosmetic composition which exhibits sufficient hair set performance and restyling performance and is free from stickiness and stiffness after hairstyling.

<Method for Measuring Weight Average Molecular Weight>

In the present invention, the weight average molecular weight of the component (A), the component (B) and another polymer is defined as a value in terms of polystyrene measured by gel permeation chromatography (GPC).

[(A): Oxyalkylene Polymer]

In the formula (a1), from the viewpoint of attaining sufficient self-selective-adhesiveness after drying the hair cosmetic composition, n is preferably 50 or more, more preferably 100 or more, still more preferably 150 or more, still more preferably 250 or more, and further preferably 1,000 or more. Furthermore, from the viewpoint of showing sufficient self-selective-adhesiveness after drying the hair cosmetic composition and avoiding usability degradation accompanying viscosity increase of the composition, n is preferably 30,000 or less, more preferably 12,000 or less, still more preferably 4,000 or less, still more preferably 3,000 or less and further preferably 2,500 or less.

Also in the formula (a1), A represents an alkylene group having 2 to 6 carbon atoms, and n pieces of AO comprise a combination of at least two alkyleneoxy groups. The n pieces of AO preferably include a combination of two or more alkyleneoxy groups each having 2 to 4 carbon atoms, and more preferably a combination of alkyleneoxy groups respectively having 2 carbon atoms and 3 carbon atoms, namely, a combination of an ethyleneoxy group and a propyleneoxy group. Furthermore, the arrangement form of two or more AO in $(AO)_n$ may be either random polymerization or block polymerization.

In the oxyalkylene polymer as the component (A), from the viewpoint of showing the self-selective-adhesiveness after drying the hair cosmetic composition, the content of a propyleneoxy group in the entire component (A) is preferably 1% by mass or more, more preferably 3% by mass or more, still more preferably 5% by mass or more and further preferably 10% by mass or more. Furthermore, from the viewpoint of attaining excellent solubility in water and attaining sufficient self-selective-adhesiveness after drying the hair cosmetic composition, the content of the propyleneoxy group in the entire component (A) is preferably 60% by mass or less, more preferably 50% by mass or less, still more preferably 40% by mass or less, still more preferably 30% by mass or less and further preferably 15% by mass or less.

From the viewpoint of attaining sufficient self-selective-adhesiveness after drying the hair cosmetic composition, the oxyalkylene polymer as the component (A) has a weight average molecular weight of preferably 3,000 or more, more preferably 5,000 or more, still more preferably 7,000 or more, still more preferably 10,000 or more and further preferably 50,000 or more. Furthermore, from the viewpoint of showing sufficient self-selective-adhesiveness after drying the hair cosmetic composition and avoiding usability degradation accompanying viscosity increase, the weight average molecular weight is preferably 1,500,000 or less, more preferably 600,000 or less, still more preferably 200,000 or less, still more preferably 150,000 or less and further preferably 100,000 or less.

A method for preparing the component (A) is not especially limited, but the component (A) is preferably prepared through ring opening polymerization of a cyclic compound comprising oxygen such as alkyleneoxide, and either a basic catalyst or an acid catalyst may be used as a catalyst for the polymerization.

A content of the oxyalkylene polymer as the component (A) in the hair cosmetic composition of the present invention (a content of a stock solution as for an aerosol product; the same shall apply hereinafter) is preferably 0.01% by mass or more, more preferably 0.05% by mass or more, still more preferably 0.1% by mass or more, still more preferably 0.5% by mass or more and further preferably 1% by mass or more from the viewpoint of attaining excellent styling performance and hairstyle retention after drying the hair cosmetic composition. Furthermore, from the viewpoint of securing appropriate styling easiness, the content is preferably 20% by mass or less, more preferably 15% by mass or less, still more preferably 10% by mass or less and further preferably 5% by mass or less.

[(B): Polymer Comprising Constitutional Units (b1) and (b2)]

Even though the hair cosmetic composition of the present invention does not show adhesiveness before application to hair, it shows self-selective-adhesiveness when dried after application. For this purpose, it is necessary for the component (B) to be in a state dispersed in water in the hair cosmetic composition. Besides, it is necessary that after the hair cosmetic composition is applied to the hair, drying of the cosmetic results in homogeneously mixed component (A) and the component (B) and shows the self-selective-adhesiveness. In order to achieve such a feature, the structure of the component (B) is specified as follows.

In the polymer comprising the constitutional units (b1) and (b2), from the viewpoint that the hair cosmetic composition shows the self-selective-adhesiveness after applying the hair cosmetic composition to hair and drying it, is excellent in the hair set performance and the restyling performance and is free from stiffness, most of the constitutional unit (b1) needs to be present as an unneutralized acid type component. The constitutional unit (b1) may be partly neutralized, but from the viewpoint of showing the self-selective-adhesiveness, it is necessary for the hair cosmetic composition to have a pH of 6 or less, preferably 5.9 or less and more preferably 5.8 or less. On the other hand, from the viewpoint of attaining excellent self-selective-adhesiveness after drying the hair cosmetic composition, the hair cosmetic composition preferably has a pH of 2 or more, more preferably 2.5 or more, still more preferably 3 or more and further preferably 3.5 or more. Besides, in the polymer as the component (B), an equivalent ratio of a base used for neutralization to a carboxy group present in the unneutralized acid type component is preferably 0 to 40%, more preferably 0 to 20% and still more preferably 0 to 10%.

The substituents $R^1$ and $R^2$ of the constitutional units (b1) and (b2) represent a hydrogen atom or a methyl group. The substituent $R^3$ represents a hydrocarbon group having 1 to 30 carbon atoms, and the hydrocarbon group may be either saturated or unsaturated and either straight or branched. The carbon pieces of the substituent $R^3$ is preferably 2 or more from the viewpoint of making the hair cosmetic composition less sticky, and is preferably 18 or less, more preferably 16 or less and still more preferably 12 or less from the viewpoint of attaining excellent dispersibility of the component (B) in water phase.

Besides, an acid value of the component (B) is 5 or more, preferably 30 or more, more preferably 65 or more and still more preferably 100 or more from the viewpoint of attaining good self-selective-adhesiveness after drying the hair cosmetic composition. Furthermore, from the viewpoint of lowering water-solubility of the component (B) for allowing it to present in a stably dispersed state in water, the acid value of the component (B) is 400 or less, preferably 370 or less, more preferably 360 or less, still more preferably 325 or less, and further preferably 180 or less.

Incidentally, as the acid value of the component (B), if a catalog value is known, the catalog value is used. If a catalog value is not found, the acid value is obtained by a third method described in "28. Sanka Sokutei Ho (Method for Measuring Acid Value in Japanese)" of The Japanese Standards of Quasi-Drug Ingredients 2006 I (published by Yakuji Nippo Ltd.).

From the viewpoint that the component (B) has the aforementioned acid value to attain good self-selective-adhesiveness, a mass ratio between the constitutional units (b1) and (b2) of the component (B), (b1)/(b2), is preferably 1/99 or more, more preferably 3/97 or more, and still more preferably 8/92 or more, and preferably 49/51 or less, more preferably 45/55 or less, and still more preferably 41/59 or less.

The mass ratio between the constitutional units (b1) and (b2) of the component (B) can be calculated on the basis of amounts used in synthesizing the polymer, and can also be calculated based on the molecular weight of the constitutional unit (b1) and the acid value of the component (B). If a commercially available polymer is used as the component (B), the ratio (b1)/(b2) is preferably calculated in accordance with the following equations by using the molecular weight of the constitutional unit (b1) and the acid value of the component (B).

(Mass % of unit (b1) in component (B))=(acid value of component (B))/1000/56.11×(molecular weight of unit (b1))×100

(Mass % of unit (b2) in component (B))=100−(mass % of unit (b1) in component (B))

Ratio (b1)/(b2)=(mass % of unit (b1) in component (B))/(mass % of unit (b2) in component (B))

Furthermore, from the viewpoint of attaining good self-selective-adhesiveness, the component (B) is preferably a non-crosslinked polymer.

Besides, the polymer of the component (B) may contain another constitutional unit in addition to the units (b1) and (b2), but such a constitutional unit is preferably contained in a ratio of preferably 30% by mass or less of the entire component (B), more preferably 20% by mass or less, still more preferably 15% by mass or less, and further preferably 10% by mass or less. Alternatively, the polymer may not contain another constitutional unit in addition to the units (b1) and (b2). Examples of the constitutional unit other than the constitutional units (b1) and (b2) include: nonionic constitutional units derived from compounds having a vinyl structure such as vinyl pyrrolidone, vinyl caprolactam and vinyl acetate and compounds having structures of alkylacrylamide, N,N-dialkylacrylamide, hydroxyalkyl (meth)acrylate, alkoxy PEG (meth)acrylate and the like; cationic constitutional units derived from compounds such as N,N-dimethylaminopropyl acrylamide and dimethylaminoethyl acrylamide; anionic constitutional units derived from monocarboxylic acids other than (meth)acrylic acid such as crotonic acid, dicarboxylic acids such as itaconic acid, maleic acid and fumaric acid, sulfonic acids such as vinyl sulfonic acid, and phosphoric acids such as acryloyloxyethyl phosphate; and amphoteric constitutional units derived from compounds having structures of carboxybetaine, sulfobetaine, phosphobetaine and the like.

A method for preparing the component (B) is not especially limited, and the polymer may be prepared by polymerizing an acrylic monomer capable of forming the constitutional units by existing polymerization, such as radical polymerization, living polymerization, living radical polymerization, group-transfer polymerization and ring opening polymerization. The structure type of the polymer employed in this case is not especially limited and may be any one of a random polymer, a block polymer and a graft polymer, and is preferably a random polymer from the viewpoint of showing sufficient self-selective-adhesiveness together with the oxyethylene polymer.

The component (B) has a weight average molecular weight of preferably 5,000 or more, more preferably 7,000 or more and still more preferably 10,000 or more from the viewpoint of attaining excellent self-selective-adhesiveness after drying the hair cosmetic composition. Besides, the weight average molecular weight is preferably 1,000,000 or less, more preferably 800,000 or less and still more preferably 600,000 or less from the viewpoint of suppressing hardening of a film formed on hair for attaining excellent restyling performance.

Preferable examples of the polymer of the component (B) include Luvimer 100P (BASF Japan Ltd., INCI name: Acrylates Copolymer), Luvimer Pro55 (BASF Japan Ltd., INCI name: Acrylates Copolymer), Luviflex Soft (BASF Japan Ltd., INCI name: Acrylates Copolymer), Luvigel FIT (BASF Japan Ltd., INCI name: Acrylates/C10-C30 methacrylate copolymer), and Daitosol 5000SL (Daito Kasei Kogyo Co., Ltd., INCI name: Acrylates Copolymer).

A content of the component (B) in the hair cosmetic composition of the present invention is preferably 0.01% by mass or more, more preferably 0.05% by mass or more, still more preferably 0.1% by mass or more, still more preferably 0.5% by mass or more and further preferably 1% by mass or more from the viewpoint of attaining excellent styling performance and hairstyle retention after drying the hair cosmetic composition. Besides, from the viewpoint of attaining appropriate styling easiness, the content is preferably 20% by mass or less, more preferably 15% by mass or less, still more preferably 10% by mass or less and further preferably 5% by mass or less.

A mass ratio (A)/(B) between the component (A) and the component (B) in the hair cosmetic composition of the present invention is preferably 25/75 or more, more preferably 35/65 or more, and still more preferably 40/60 or more from the viewpoint of attaining good self-selective-adhesiveness through interaction between the component (A) and the component (B) after drying the hair cosmetic composition. Besides, from the viewpoint of attaining excellent self-selective-adhesiveness after drying the hair cosmetic composition, the mass ratio is preferably 70/30 or less, more preferably 65/35 or less and still more preferably 60/40 or less.

[Another Set Polymer]

When another set polymer is contained as an arbitrary component in addition to the components (A) and (B) in the hair cosmetic composition of the present invention, the set retention may be further improved. Examples of such a set polymer include (methacryloyloxyethyl carboxybetaine/ alkyl methacrylate) copolymers such as YUKAFORMER R205 and YUKAFORMER 301 (both manufactured by Mitsubishi Chemical Corporation) and RAM resin (manufactured by Osaka Organic Chemical Industry Ltd.); (acrylate/lauryl acrylate/stearyl acrylate/ethylamine oxide methacrylate) copolymers such as DIAFORMER Z-651 (manufactured by Mitsubishi Chemical Corporation); acrylic acid/acrylic acid amide/ethyl acrylate copolymers such as Ultrahold 8 and Ultrahold Strong (both manufactured by BASF Japan Ltd.); alkyl acrylate/methacrylic acid/ silicone copolymers such as Luviflex Silk (manufactured by BASF Japan Ltd.); polyurethane such as Luviset P.U.R (manufactured by BASF Japan Ltd.); polyvinyl caprolactam such as Luviskol Plus (manufactured by BASF Japan Ltd.); (octylacrylamide/hydroxypropyl acrylate/butylaminoethyl methacrylate) copolymers such as Unfoamer 28-4910 and Unfoamer LV-71 (both manufactured by Akzo Nobel); (alkyl acrylate/octylacrylamide) copolymers such as Unfoamer HC (manufactured by Akzo Nobel); (vinyl acetate/crotonic acid/vinyl neodecanoate) copolymers such as Resin 28-2930 (manufactured by Akzo Nobel); polyurethane 14/AMP-acrylate copolymers such as DynamX (manufactured by Akzo Nobel); (PVP/vinyl caprolactam/ DMAPA acrylate) copolymers such as Aquaflex SF-40 (manufactured ISP Japan Ltd.); (isobutylene/ethyl maleimide/hydroxyethyl maleimide) copolymers such as Aquaflex FX-64 (manufactured by ISP Japan Ltd.); (vinyl pyrrolidone/DMAPA acrylate) copolymers such as Styleze CC-10 (manufactured by ISP Japan Ltd.); and (vinyl pyrrolidone/ vinyl acetate) copolymers such as PVP/VA E-735 (manufactured by ISP Japan Ltd.) and Luviskol VA64P (manufactured by BASF Japan Ltd.).

Of the aforementioned set polymers, the acrylic acid/ acrylic acid amide/ethyl acrylate copolymers, the alkyl acrylate/methacrylic acid/silicone copolymers, polyurethane, the (methacryloyloxyethyl carboxybetaine/alkyl methacrylate) copolymers, the (octylacrylamide/hydroxypropyl acrylate/ butylaminoethyl methacrylate) copolymers, the acrylic acid/ acrylic acid amide/alkyl acid ethyl copolymers, polyvinyl caprolactam and the (alkyl acrylate/octylacrylamide) copolymers are preferably used, and the acrylic acid/acrylic acid amide/ethyl acrylate copolymers and polyurethane are more preferably used for further improving selective adhesiveness. Two or more of such set polymers other than the components (A) and (B) may be used in combination.

From the viewpoint of retaining a merit of excellent self-selective-adhesiveness of the hair cosmetic composition of the present invention, the content of such a set polymer is set so that a mass ratio between the total amount of the components (A) and (B) and the amount of another set polymer, i.e. [(A)+(B)]/[another set polymer], can be preferably 60/40 or more, more preferably 70/30 or more and still more preferably 80/20 or more. Besides, the mass ratio is preferably 99/1 or less, and more preferably 97/3 or less.

[Medium]

The hair cosmetic composition of the present invention contains water as a support medium, and lower alcohols (such as ethanol and isopropanol), lactones and the like may be used together, and these may be singly used or mixedly used. From the viewpoint of certainly attaining dispersibility of the component (B), water, or a mixed system of water and ethanol is preferably used. Besides, a content of a solvent other than water is preferably 20% by mass or less, more preferably 10% by mass or less, and still more preferably 5% by mass or less from the viewpoint of certainly attaining the dispersibility of the component (B).

[Arbitrary Component]

Apart from the aforementioned components, a plasticizer component can be contained in the hair cosmetic composition of the present invention for the purpose of providing appropriate adhesiveness and re-adhesiveness without harming the self-selective-adhesiveness. Examples of such a plasticizer component include polyalcohols such as glycerin, 1,3-butanediol and dipropylene glycol, and nonionic surfactants.

Furthermore, a cosmetic oil component may be added within a limit not impeding the effects of the present invention (in 0.1 to 10% by mass). Examples of the cosmetic oil component include glycerides such as castor oil, cacao oil, mink oil, avocado oil and olive oil; waxes such as bees wax, spermaceti wax, lanolin and carnauba wax; higher alcohols such as cetyl alcohol, oleyl alcohol, hexadecyl alcohol, lauryl alcohol, stearyl alcohol, isostearyl alcohol and 2-octyldodecanol; esters such as isopropyl myristate, hexyl laurate, cetyl lactate, propylene glycol monostearate, oleyl oleate, hexadecyl 2-ethylhexanoate and octyldodecyl myristate; hydrocarbon oils such as liquid paraffin, vaseline, squalene and hydrogenated polyisobutene; and silicone derivatives such as dimethylpolysiloxane, methylphenylpolysiloxane, polyether-modified silicone oil, epoxy-modified silicone oil, amino-modified silicone oil and alkyl-modified silicone oil. Furthermore, an emulsifier may be added for emulsion stabilizing the cosmetic oil component. As the emulsifier, any of anionic, amphoteric, cationic and nonionic surfactants can be used.

Moreover, the hair cosmetic composition of the present invention may contain a perfume or a dye for increasing its commercial value, and an antiseptic agent or an antioxidant for preventing quality deterioration over time of the hair cosmetic composition. Besides, the hair cosmetic composition may contain a moisture controlling agent, a curing agent, an antistatic agent, an antifoamer, a dispersant, a thickening agent, an ultraviolet absorber, a coloring dye, a dye fixative, a propellant and the like if necessary.

[Dosage Form]

The dosage form of the hair cosmetic composition of the present invention is not especially limited, and the hair cosmetic composition may be in the form of, for example, a transparent liquid, a lotion, an emulsion, a spray (aerosol or non-aerosol) or a foam (aerosol or non-aerosol).

An aerosol hair cosmetic composition is produced by filling the aforementioned hair cosmetic composition together with a propellant in a pressure-resistant container. Examples of the propellant include liquefied petroleum gas (LPG), dimethyl ether (DME), a carbon dioxide gas, a nitrogen gas, and a mixture of these. Alternatively, alternative freon such as HFC-152a may be used. From the viewpoint of attaining excellent spraying performance and excellent adhesion characteristics, the amount of the propellant is, in terms of a mass ratio between a stock solution and the propellant, i.e., a stock solution/propellant ratio, of 5/95 to 99/1 and more preferably 20/80 to 95/5. For attaining excellent spraying performance and excellent adhesion characteristics, the pressure within the pressure-resistant container is preferably adjusted to 0.12 to 0.45 MPa at a temperature of 25° C.

[Hair Styling Method]

The hair cosmetic composition of the present invention can be suitably used as a hair styling agent. The hair cosmetic composition of the present invention is a composition which is not adhesive before application to hair, but slowly shows adhesiveness while a hairstyle is being set after applying and spreading it on the hair. Therefore, when it is applied to the hair or the hair is set with a hair brush or the like, it can be easily uniformly applied over the entire hair, and the hair brush is not entangled, and therefore, the hair can be freely handled for hair setting. On the other hand, when the hair cosmetic composition is dried after setting the hair, the hair cosmetic composition forms a firm transparent film having the self-selective-adhesiveness, and the hairs can be retained with strong adhesiveness. Therefore, a method for using the hair cosmetic composition of the present invention as a hair styling agent, namely, a hair styling method, preferably includes the steps of: i) applying the hair cosmetic composition of the present invention to hair; and ii) then setting a hairstyle. The hair cosmetic composition of the present invention may be applied to wet hair or to dry hair.

Besides, in setting the hairstyle in the step ii), the hair is set preferably while applying heat. For example, after drying wetted hair with a towel, the hair cosmetic composition of the present invention is applied to the hair, and the hair is preferably dried and set by using a hair iron or a hair dryer. Furthermore, if the hair is dried and set by using a hair iron or a hair dryer in the step ii), the hair is set more preferably while combing with a hair brush or a comb. In this manner, the hair may be effectively styled, and the set hairstyle can be retained.

Besides, a step of drying the wetted hair with a towel may be performed before the step i). Thereafter, the hair cosmetic composition of the present invention is uniformly applied to the whole hair from the hair roots or the inside of the hair in the step i) and drying the hair with a hair dryer in the step ii), and thus, hair volume in appearance and feel can be preferably increased.

Moreover, after setting a hairstyle with the hair cosmetic composition of the present invention applied to the hair, the set hairstyle may be changed or restyled if the hairstyle is disarranged, without using a hair dryer or a hair iron. The hair styling thus performed after setting the hairstyle once can be easily conducted with fingers.

With respect to the embodiment of the hair cosmetic composition described so far, preferable aspects will now be further described below.

<1> A hair cosmetic composition comprising the following components (A), (B) and water, having a pH at 25° C. of 6 or less, and the component (B) being dispersed in a water phase:

(A) an oxyalkylene polymer represented by the following formula (a1):

—(AO)$_n$—       (a1)

wherein A represents an alkylene group having 2 to 6 carbon atoms and n represents a number of 50 or more and 30,000 or less, provided that n pieces of AO comprise at least two alkyleneoxy groups, which are arranged through either random polymerization or block polymerization; and (B) a polymer comprising a constitutional unit represented by the following formula (b1) and a constitutional unit represented by the following formula (b2), having a weight average molecular weight of 5,000 or more and 1,000,000 or less, and having an acid value of a solid content of 5 or more and 400 or less:

—(CH$_2$CR$^1$COOH)—       (b1)

—(CH$_2$CR$^2$COOR$^3$)—       (b2)

wherein R$^1$ and R$^2$ represent a hydrogen atom or a methyl group and R$^3$ represents a hydrocarbon group having 1 or more and 30 or less carbon atoms.

<2> The hair cosmetic composition according to <1>, in which the oxyalkylene polymer of the component (A) has a weight average molecular weight of preferably 3,000 or more, more preferably 5,000 or more, still more preferably 7,000 or more, still more preferably 10,000 or more, and further preferably 50,000 or more, and preferably 1,500,000 or less, more preferably 600,000 or less, still more preferably 200,000 or less, still more preferably 150,000 or less, and further preferably 100,000 or less.

<3> The hair cosmetic composition according to <1> or <2>, in which n pieces of AO contained in the component (A) include preferably a combination of two or more alkyleneoxy groups each having 2 to 4 carbon atoms, and more preferably a combination of an ethyleneoxy group and a propyleneoxy group.

<4> The hair cosmetic composition according to any one of <1> to <3>, in which a content of a propyleneoxy group in the entire component (A) is preferably 1% by mass or more, more preferably 3% by mass or more, still more preferably 5% by mass or more, and further preferably 10% by mass or more, and preferably 60% by mass or less, more preferably 60% by mass or less, still more preferably 50% by mass or less, still more preferably 40% by mass or less, still more preferably 30% by mass or less, and further preferably 15% by mass or less.

<5> The hair cosmetic composition according to any one of <1> to <4>, in which a weight average molecular weight of the polymer of the component (B) is preferably 7,000 or more, and more preferably 10,000 or more, and preferably 800,000 or less, and more preferably 600,000 or less.

<6> The hair cosmetic composition according to any one of <1> to <5>, in which a content of the component (A) is preferably 0.01% by mass or more, more preferably 0.05% by mass or more, still more preferably 0.1% by mass or more, still more preferably 0.5% by mass or more, and further preferably 1% by mass or more, and preferably 20% by mass or less, more preferably 15% by mass or less, still more preferably 10% by mass or less, and further preferably 5% by mass or less.

<7> The hair cosmetic composition according to any one of <1> to <6>, in which a content of the component (B) is preferably 0.01% by mass or more, more preferably 0.05% by mass or more, still more preferably 0.1% by mass or more, still more preferably 0.5% by mass or more, and further preferably 1% by mass or more, and preferably 20% by mass or less, more preferably 15% by mass or less, still more preferably 10% by mass or less, and further preferably 5% by mass or less.

<8> The hair cosmetic composition according to any one of <1> to <7>, in which n in the formula (a1) representing the component (A) is preferably 100 or more, more preferably 150 or more, still more preferably 250 or more, and further preferably 1,000 or more, and preferably 12,000 or less, more preferably 4,000 or less, still more preferably 3,000 or less, and further preferably 2,500 or less.

<9> The hair cosmetic composition according to any one of <1> to <8>, in which the hair cosmetic composition has a pH of preferably 5.9 or less, and more preferably 5.8 or less, and preferably 2.0 or more, more preferably 2.5 or more, still more preferably 3 or more and further preferably 3.5 or more.

<10> The hair cosmetic composition according to any one of <1> to <9>, in which R$^3$ of the formula (b2) of the component (B) has a carbon number of preferably 2 or more, and preferably 18 or less, more preferably 16 or less and still more preferably 12 or less.

<11> The hair cosmetic composition according to any one of <1> to <10>, in which the component (B) has an acid value of preferably 30 or more, more preferably 65 or more and still more preferably 100 or more, and preferably 370 or less, more preferably 360 or less, still more preferably 325 or less, and further preferably 180 or less.

<12> The hair cosmetic composition according to any one of <1> to <11>, in which a mass ratio (A)/(B) between the component (A) and the component (B) is preferably 25/75 or more, more preferably 35/65 or more and still more preferably 40/60 or more, and preferably 70/30 or less, more preferably 65/35 or less and still more preferably 60/40 or less.

<13> The hair cosmetic composition according to any one of <1> to <12>, in which a mass ratio of a constitutional unit contained, in addition to the constitutional units (b1) and (b2), in the polymer of the component (B) is preferably 30% by mass or less, more preferably 20% by mass or less, still more preferably 15% by mass or less, and further preferably 10% by mass or less.

<14> The hair cosmetic composition according to any one of <1> to <13>, in which a mass ratio between the constitutional units (b1) and (b2) of the component (B), (b1)/(b2), is preferably 1/99 or more, more preferably 3/97 or more and still more preferably 8/92 or more, and preferably 49/51 or less, more preferably 45/55 or less, and still more preferably 41/59 or less.

<15> The hair cosmetic composition according to any one of <1> to <14>, in which the component (B) is preferably a non-crosslinked polymer.

<16> A hair styling method comprising the steps of:
  i) applying the hair cosmetic composition according to any one of <1> to <15> to hair; and
  ii) then setting a hairstyle.

<17> The hair styling method according to <16>, in which the hair is preferably set with heat applied to the hair in setting the hairstyle in step ii).

<18> The hair styling method according to <16> or <17>, in which the hair is preferably set while combing the hair with a hair brush or a comb in setting the hairstyle in step ii).

<19> Use of the hair cosmetic composition according to any one of <1> to <15> as a hair styling agent.

EXAMPLES

In examples described below, the weight average molecular weight of each polymer and the acid value of a polymer used as the component (B) were measured by the following methods.

<Method for Measuring Weight Average Molecular Weight>

If a catalog value or the like is not known and hence it is necessary to measure the weight average molecular weight, the measurement was performed by using, as a GPC apparatus, an apparatus available under a trade name "HLC-8220GPC" (manufactured by Tosoh Corporation) under the following measurement conditions:

In measurement for a polymer different from the component (B):
  Sample concentration: 0.25% by mass
  Sample amount: 100 µL
  Eluent: chloroform
  Flow rate: 1.0 mL/min
  Measurement temperature: 40° C.
  Column: three columns of trade name "K-G" (one column) and trade name "K-804L" (two columns) (both manufactured by Shodex) connected to one another for analysis In measurement for a polymer used as the component (B):
  Sample concentration: 0.25% by mass
  Sample amount: 100 µL
  Eluent: N,N-dimethylformamide solution (60 mmol/L $H_3PO_4$, 50 mmol/L LiBr)
  Flow rate: 1.0 mL/min
  Measurement temperature: 40° C.
  Column: trade name "TSKgel α-M" (two columns) (manufactured by Tosoh Corporation) connected to each other for analysis Furthermore, a detector and a standard sample were as follows in either measurement conditions:
  Detector: differential refractometer (attached to the GPC apparatus, trade name "HLC-8220GPC" (manufactured by Tosoh Corporation))
  Polystyrene standard sample: "TSK standard POLYSTYRENE F-10" (molecular weight: 102,000), "F-1" (molecular weight: 10,200), "A-1000" (molecular weight: 870) (all manufactured by Tosoh Corporation), and "POLYSTYRENE STANDARD" (molecular weight: 900,000 or 30,000; manufactured by Nishio Kogyo KK)

<Method for Measuring Acid Value>

If a catalog value or the like was not known and it was necessary to measure the acid value of the component (B), the measurement was performed in accordance with an acid value measurement method (a second method) described in The Japanese Standards of Quasi-Drug Ingredients 2006. If the component (B) is a solution or a dispersion, the acid value of the solution or the dispersion was measured, and the acid value of the polymer was calculated in accordance with the concentration of the component (B) by using the following calculation equation:

Acid value of polymer=acid value of polymer solution or dispersion/concentration of polymer (%)×100

Synthesis Example 1

Synthesis of Alkyl Acrylate/Acrylic Acid (*8) Used in Comparative Example 6

A 500 mL glass separable flask equipped with a Teflon (trademark) crescent-shaped stirring blade, a reflux condenser and a thermometer was charged with 82.1 g of isopropyl alcohol. Next, after reducing the pressure within the reaction vessel to 20 kPa, a purging operation of blowing nitrogen at normal pressure was performed three times. Thereafter, the flask was dipped in an oil bath to heat the reaction solution to 80° C. with stirring at 100 rpm. After confirming the temperature increase, a mixed solution of 180.9 g of 98 mass % acrylic acid, 89.1 g of stearyl acrylate and 73.4 g of isopropyl alcohol, and a mixed solution of 1.44 g of dimethyl 2,2'-azobis(2-methylpropionate) and 13.0 g of isopropyl alcohol were separately added in a dropwise manner to the reaction solution over 4 hours. The resultant was stirred for 1 hour with the internal temperature kept at 80° C., and then, a mixed solution of 0.72 g of dimethyl 2,2'-azobis(2-methylpropionate) and 6.5 g of isopropyl alcohol was added in a dropwise manner to the reaction solution over 30 minutes. The resultant was stirred further for 6 hours with the internal temperature kept at 80° C., and then the resultant reaction solution was cooled to room temperature. Subsequently, the isopropyl alcohol was distilled off to obtain a polymer. The thus obtained polymer had an acid value of 472 and a weight average molecular weight of 14,000.

Examples 1 to 15 and Comparative Examples 1 to 6

Compositions shown in Tables 1 and 2 were prepared by a usual method. Incidentally, a pH of each composition was controlled to a specified pH at 25° C. by a usual method using 2-aminomethyl propanol (AMP) and lactic acid. These compositions were evaluated by the following evaluation methods.

<Appearance of Composition>

20 g of each composition was put in a transparent screw vial No. 6 manufactured by Maruemu Corporation, paper having a pattern of alternate black and white stripes at an interval of 4 mm was placed behind the screw vial, and it was determined, based on the following criteria, whether or not the striped pattern behind could be seen when the composition was seen from the front:

Cloudy: The composition is cloudy and hence the striped pattern cannot be seen.

Slightly cloudy: The composition is cloudy but the striped pattern can be seen.

Transparent: The composition is not cloudy and the striped pattern can be seen.

<Evaluation Methods for Film Transparency and Self-adhesive Force/Other-adhesive Force>

A film was formed by applying 0.4 g of each composition onto a region of 30 mm×20 mm on a biaxial oriented PET film (manufactured by Toray Industries, Inc.; Lumirror L-38-T60) and allowing the resultant to stand at 25° C. and 40% RH for 24 hours to be dried. The resultant film thus formed on the PET film was evaluated for the transparency, the self-adhesive force and the other-adhesive force of the film under an environment of 25° C. and 40 to 65% RH by the following methods.

(Film Transparency)

The evaluation was performed by seven panelists, a document having a text printed in 6-point Mincho characters was placed 1 cm below the dry cast film formed on the PET film, and with respect to the characters below the film seen from the above, each panelist was requested to alternatively select one of "the characters can be clearly read", "the characters are blurred but can be read" and "the characters are too blurred to read". The numbers of panelists having selected "the characters can be clearly read."/"the characters are blurred but can be read."/"the characters are too blurred to read." are shown in this order.

(Self-adhesive Force)

Each dry cast film on the PET film is adhered to itself with a force of 1 g/cm$^2$, and a resisting force arising in peeling it at a peeling rate of 30 mm/sec in T-shape peeling mode 1 second after the adhesion was sensory evaluated to be scored in 5 grades on the assumption that the self-adhesive force attained in Example 1 was scored as 5 and that attained in Comparative Example 1 was scored as 1.

(Other-adhesive Force)

Each dry cast film was pressed down with a finger with a force of 1 g/cm$^2$, and a resisting force arising in taking the finger off at 100 mm/s 0.1 second after pressing was sensory evaluated to be scored in 5 grades on the assumption that the other-adhesive force attained in Comparative Example 3 was scored as 5 and that attained in Example 1 was scored as 1.

<Time for Occurring Adhesiveness>

On a tress of Chinese straight hairs with a length of 25 cm and a weight of 7 g, 1.0 g of each composition was applied and lightly spread, and thereafter, the resultant tress was blow-dried with a dryer (EH5311 manufactured by Matsushita Electric Works Ltd.) set at a distance of 20 cm while finger combing once every second, and a time (in sec) elapsing until adhesiveness to fingers was felt was defined as a time for occurring adhesiveness.

If the time elapsing until the adhesiveness occurs is 15 seconds or more, a hairstyle can be sufficiently deliberately set.

<Evaluation of Styling Performance>

A tress of Chinese straight hairs with a length of 25 cm and a weight of 3 g was wetted with water and dried with a towel, and thereafter, 1 g of each composition was applied thereon, and the tress was set by drying with a dryer for 1 minute while curling the tress inward by finger combing. The thus set tress was evaluated from the viewpoint whether or not the hair stream was evenly arranged and the hair could be curled as desired without minutely protruding. Seven panelists were requested to alternatively select, in treating the tress with each composition in the aforementioned manner, whether the hair setting was "easy", "neither easy nor difficult" or "difficult" to perform. The numbers of panelists having selected "easy"/"neither easy nor difficult"/"difficult" are shown in this order.

<Evaluation of Restyling Performance>

The tress for evaluation curled by finger combing for use in the evaluation for the styling performance was combed five times with a comb (Delrin Smooth Comb #802 (straight); Takigawa Co., Ltd.) so as to disarrange the set style of the tress, and thereafter, an operation to restore, with fingers, the tress again into the original style obtained before the combing was performed. The tress obtained after this operation was evaluated from the viewpoint whether or not the tress was restored into the original style without losing curls and minutely protruding. Seven panelists were requested to alternatively select, in performing the above-described operation, whether the restyling was "easy", "neither easy nor difficult" or "difficult" to perform. The numbers of panelists having selected "easy"/"neither easy nor difficult"/"difficult" are shown in this order.

<Evaluation for Stickiness to Fingers after Hairstyling>

With respect to the feel of the tress having been thus set, seven panelists were requested to select one of "not sticky", "difficult to say which" and "sticky". The numbers of panelists having selected "not sticky"/"difficult to say which"/"sticky" are shown in this order.

<Evaluation for Stiffness after Hairstyling>

With respect to the feel of the tress having been thus set, seven panelists were requested to select one of "not stiff", "difficult to say which" and "stiff". The numbers of panelists having selected "not stiff"/"difficult to say which"/"stiff" are shown in this order.

Notes (*0 to *8) given in Tables 1 and 2 are as follows:

*0: weight average molecular weight: 2,200, EO/PO mass ratio=20/80, block polymerization (Sanyo Kasei Co., Ltd., New Pol PE-62)

(degree of polymerization calculated based on EO/PO mass ratio: EO=10, PO=30)

*1: weight average molecular weight: 100,000, EO/PO mass ratio=90/10, random polymerization (Meisei Chemical Works Ltd., EP1010N)

(degree of polymerization calculated based on EO/PO mass ratio: EO=2,000, PO=200)

*2: weight average molecular weight: 16,000, EO/PO mass ratio=80/20, block polymerization (Sanyo Kasei Co., Ltd., New Pol PE-108)

(degree of polymerization calculated based on EO/PO mass ratio: EO=300, PO=55)

*3: weight average molecular weight: 5,000, EO/PO mass ratio=70/30, random polymerization (ADEKA Corporation, Adeka polyether PR5007)

(degree of polymerization calculated based on EO/PO mass ratio: EO=80, PO=26)

*4: weight average molecular weight: 3,400, EO/PO mass ratio=40/60, block polymerization (Sanyo Kasei Co., Ltd., New Pol PE-74)

(degree of polymerization calculated based on EO/PO mass ratio: EO=30, PO=35)

*5: $R^3$=t-Bu, Et, acid value: 122 to 162, weight average molecular weight: 60,000, $R^1$=Me, $R^2$=H (BASF Japan Ltd., Luvimer Pro55)

*6: $R^3$=Et, acid value: 283 to 350, weight average molecular weight: 500,000, $R^1$=Me, $R^2$=H (BASF Japan Ltd., Luviflex Soft)

*7: $R^3$=C2-C22 alkyl, acid value: 283 to 350, $R^1$=$CH_3$, $R^2$=H, $CH_3$ (BASF Japan Ltd., Luvigel FIT)

*8: $R^3$=$C_{18}$ alkyl, acid value: 472, weight average molecular weight: 14,000, $R^1$, $R^2$=H

TABLE 1

| (% by mass; all in terms of amount of active portion) | | | Example 1 | Example 2 | Example 3 | Example 4 | Example 5 | Example 6 |
|---|---|---|---|---|---|---|---|---|
| (A) | | Oxyalkylene polymer (*1) | 1.2 | 1.2 | 1.2 | — | — | — |
| | | Oxyalkylene polymer (*2) | — | — | — | 1.2 | 1.2 | — |
| | | Oxyalkylene polymer (*3) | — | — | — | — | — | 1.2 |
| | | Oxyalkylene polymer (*4) | — | — | — | — | — | — |
| (B) | | Alkyl acrylate/acrylic acid copolymer (*5) | 1.8 | — | — | 1.8 | — | 1.8 |
| | | Alkyl acrylate/acrylic acid copolymer (*6) | — | 1.8 | — | — | 1.8 | — |
| | | Alkyl acrylate/acrylic acid copolymer (*7) | — | — | 1.8 | — | — | — |
| (B') | | Alkyl acrylate/acrylic acid copolymer (*8) | — | — | — | — | — | — |
| Other components | | AMP | — | q.s. | q.s. | — | q.s. | — |
| | | Lactic acid | q.s. | — | — | q.s. | — | q.s. |
| | | Purified Water | balance | balance | balance | balance | balance | balance |
| | | pH of formulation | 4.5 | 4.5 | 4.5 | 4.5 | 4.5 | 4.5 |
| | | Mass ratio (A)/(B) | 40/60 | 40/60 | 40/60 | 40/60 | 40/60 | 40/60 |
| Evaluation | | Appearance of composition | cloudy | cloudy | cloudy | cloudy | cloudy | cloudy |
| | | Self-adhesive force (organoleptic score) | 5 | 5 | 4 | 5 | 5 | 5 |
| | | Other-adhesive force (organoleptic score) | 1 | 1 | 1 | 1 | 1 | 2 |
| | | Film transparency | 7/0/0 | 7/0/0 | 7/0/0 | 7/0/0 | 7/0/0 | 7/0/0 |
| | | Time for occurring adhesiveness (sec) | 24 | 30 | 28 | 25 | 24 | 31 |
| | | Styling performance | 7/0/0 | 7/0/0 | 5/2/0 | 7/0/0 | 5/2/0 | 6/1/0 |
| | | Restyling performance | 6/1/0 | 7/0/0 | 5/2/0 | 6/1/0 | 5/2/0 | 6/1/0 |
| | | Stickiness | 7/0/0 | 6/1/0 | 6/1/0 | 7/0/0 | 6/1/0 | 5/2/0 |
| | | Stiffness | 7/0/0 | 7/0/0 | 7/0/0 | 5/2/0 | 7/0/0 | 5/1/1 |

| (% by mass; all in terms of amount of active portion) | | | Example 7 | Example 8 | Example 9 | Example 10 | Example 11 | Example 12 |
|---|---|---|---|---|---|---|---|---|
| (A) | | Oxyalkylene polymer (*1) | — | — | — | 1.8 | 1.5 | 0.9 |
| | | Oxyalkylene polymer (*2) | — | — | — | — | — | — |
| | | Oxyalkylene polymer (*3) | 1.2 | — | — | — | — | — |
| | | Oxyalkylene polymer (*4) | — | 1.2 | 1.2 | | | |
| (B) | | Alkyl acrylate/acrylic acid copolymer (*5) | — | — | — | 1.2 | 1.5 | 2.1 |
| | | Alkyl acrylate/acrylic acid copolymer (*6) | 1.8 | 1.8 | — | — | — | — |
| | | Alkyl acrylate/acrylic acid copolymer (*7) | — | — | 1.8 | — | — | — |
| (B') | | Alkyl acrylate/acrylic acid copolymer (*8) | — | — | — | — | — | — |
| Other components | | AMP | q.s. | q.s. | q.s. | — | — | — |
| | | Lactic acid | — | — | — | q.s. | q.s. | q.s. |
| | | Purified Water | balance | balance | balance | balance | balance | balance |
| | | pH of formulation | 4.5 | 4.5 | 4.5 | 4.5 | 4.5 | 4.5 |
| | | Mass ratio (A)/(B) | 40/60 | 40/60 | 40/60 | 60/40 | 50/50 | 30/70 |
| Evaluation | | Appearance of composition | cloudy | cloudy | cloudy | cloudy | cloudy | cloudy |
| | | Self-adhesive force (organoleptic score) | 4 | 4 | 4 | 5 | 5 | 3 |
| | | Other-adhesive force (organoleptic score) | 1 | 1 | 1 | 1 | 2 | 1 |
| | | Film transparency | 7/0/0 | 7/0/0 | 7/0/0 | 5/2/0 | 7/0/0 | 7/0/0 |
| | | Time for occurring adhesiveness (sec) | 34 | 28 | 25 | 26 | 26 | 22 |
| | | Styling performance | 6/1/0 | 5/2/0 | 5/2/0 | 7/0/0 | 6/1/0 | 5/1/1 |
| | | Restyling performance | 5/2/0 | 5/2/0 | 5/1/1 | 6/1/0 | 6/1/0 | 4/3/0 |
| | | Stickiness | 6/1/0 | 6/1/0 | 6/1/0 | 5/2/0 | 5/1/1 | 6/1/0 |
| | | Stiffness | 6/1/0 | 6/1/0 | 6/1/0 | 4/3/0 | 5/2/0 | 6/1/0 |

TABLE 2

| | | Example | | | Comparative Example | | | | | |
|---|---|---|---|---|---|---|---|---|---|---|
| (% by mass; all in terms of amount of active portion) | | 13 | 14 | 15 | 1 | 2 | 3 | 4 | 5 | 6 |
| (A') | Oxyalkylene polymer (*0) | — | — | — | — | — | 1.5 | 1.5 | 1.5 | — |
| (A) | Oxyalkylene polymer (*1) | 1.2 | 1.2 | 1.2 | 1.2 | 1.2 | — | — | — | 1.5 |
| | Oxyalkylene polymer (*2) | — | — | — | — | — | — | — | — | — |
| | Oxyalkylene polymer (*3) | — | — | — | — | — | — | — | — | — |
| | Oxyalkylene polymer (*4) | — | — | — | — | — | — | — | — | — |
| (B) | Alkyl acrylate/acrylic acid copolymer (*5) | — | — | — | — | — | 1.5 | — | — | — |
| | Alkyl acrylate/acrylic acid copolymer (*6) | 1.8 | 1.8 | 1.8 | 1.8 | 1.8 | — | 1.5 | — | — |
| | Alkyl acrylate/acrylic acid copolymer (*7) | — | — | — | — | — | — | — | 1.5 | — |
| (B') | Alkyl acrylate/acrylic acid copolymer (*8) | — | — | — | — | — | — | — | — | 1.5 |
| Other components | AMP | — | q.s. | q.s. | q.s. | q.s. | — | q.s. | q.s. | q.s. |
| | Lactic acid | — | — | — | — | — | q.s. | — | — | — |
| | Purified Water | balance | balance | balance | balance | balance | balance | balance | balance | balance |
| | pH of formulation | 4.1 | 5 | 6 | 7 | 8 | 4.5 | 4.5 | 4.5 | 4.6 |
| | Mass ratio (A)/(B) | 40/60 | 40/60 | 40/60 | 40/60 | 40/60 | 50/50 | 50/50 | 50/50 | 50/50 |
| Evaluation | Appearance of composition | cloudy | cloudy | cloudy | transparent | transparent | cloudy | cloudy | cloudy | transparent |
| | Self-adhesive force (organoleptic score) | 5 | 5 | 5 | 1 | 1 | 5 | 4 | 3 | 5 |
| | Other-adhesive force (organoleptic score) | 1 | 1 | 1 | 1 | 1 | 5 | 3 | 2 | 1 |
| | Film transparency | 7/0/0 | 7/0/0 | 7/0/0 | 0/2/5 | 0/1/6 | 7/0/0 | 7/0/0 | 7/0/0 | 7/0/0 |
| | Time for occurring adhesiveness (sec) | 31 | 24 | 23 | 5 | 7 | 19 | 24 | 23 | 5 |
| | Styling performance | 7/0/0 | 7/0/0 | 7/0/0 | 6/1/0 | 6/1/0 | 6/1/0 | 5/1/1 | 3/3/1 | 7/0/0 |
| | Restyling performance | 7/0/0 | 7/0/0 | 6/1/0 | 0/2/5 | 0/1/6 | 6/1/0 | 2/2/3 | 2/3/2 | 7/0/0 |
| | Stickiness | 6/1/0 | 7/0/0 | 6/1/0 | 5/1/1 | 5/1/1 | 0/2/5 | 2/3/2 | 2/3/2 | 7/0/0 |
| | Stiffness | 7/0/0 | 6/1/0 | 6/1/0 | 2/3/2 | 1/3/3 | 5/1/1 | 5/1/1 | 5/2/0 | 6/1/0 |

The invention claimed is:

1. A hair cosmetic composition comprising components (A), (B) and water, having a pH at 25° C. of 6 or less, and component (B) being dispersed in a water phase of the hair cosmetic composition:

(A) an oxyalkylene polymer represented by formula (a1):

—(AO)$_n$—     (a1)

wherein A represents an alkylene group having 2 to 6 carbon atoms and n represents a number of 50 or more and 30,000 or less, provided that n pieces of AO comprise at least two alkyleneoxy groups, which are arranged either randomly or in blocks; and (B) a polymer comprising a constitutional unit represented by formula (b1) and a constitutional unit represented by formula (b2), having a weight average molecular weight of 5,000 or more and 1,000,000 or less, and having an acid value of 5 or more and 400 or less:

—(CH$_2$CR$^1$COOH)—     (b1)

—(CH$_2$CR$^2$COOR$^3$)—     (b2)

wherein R$^1$ and R$^2$ represent a hydrogen atom or a methyl group and R$^3$ represents a hydrocarbon group having 1 or more and 30 or less carbon atoms, and wherein a mass ratio between constitutional units (b1) and (b2) of component (B), (b1)/(b2), is 1/99 or more and 49/51 or less.

2. The hair cosmetic composition according to claim 1, wherein a mass ratio of a constitutional unit present in the polymer of component (B), in addition to constitutional units (b1) and (b2), is 10% by mass or less.

3. The hair cosmetic composition according to claim 1, wherein the polymer of component (B) is a non-crosslinked polymer.

4. The hair cosmetic composition according to claim 1, wherein the oxyalkylene polymer of component (A) has a weight average molecular weight of 3,000 or more and 1,500,000 or less.

5. The hair cosmetic composition according to claim 1, wherein oxyalkylene groups of the polymer of component (A) are an ethyleneoxy group and a propyleneoxy group.

6. The hair cosmetic composition according to claim 1, wherein a content of a propyleneoxy group in the polymer of component (A) is 1% by mass or more and 60% by mass or less.

7. The hair cosmetic composition according to claim 1, wherein a mass ratio between component (A) and component (B) in the hair cosmetic composition is 25/75 or more and 70/30 or less.

8. The hair cosmetic composition according to claim 1, wherein n in formula (a1) of component (A) is 250 or more and 12,000 or less.

9. The hair cosmetic composition according to claim 1, wherein a content of component (A) in the hair cosmetic composition is 0.01% by mass or more and 20% by mass or less.

10. The hair cosmetic composition according to claim 1, wherein a content of component (B) in the hair cosmetic composition is 0.01% by mass or more and 20% by mass or less.

11. A hair styling method comprising:
   i) applying the hair cosmetic composition according to claim 1 to hair; and
   ii) then setting a hairstyle.

12. The hair cosmetic composition according to claim 1, wherein the composition is not transparent.

* * * * *